(12) United States Patent
Sanai et al.

(10) Patent No.: US 9,662,513 B2
(45) Date of Patent: May 30, 2017

(54) ULTRASONIC VIBRATION TREATMENT DEVICE

(71) Applicant: OLYMPUS CORPORATION, Tokyo (JP)

(72) Inventors: Hideo Sanai, Hachioji (JP); Yuki Kawaguchi, Koshu (JP)

(73) Assignee: OLYMPUS CORPORATION, Tokyo (JP)

( * ) Notice: Subject to any disclaimer, the term of this patent is extended or adjusted under 35 U.S.C. 154(b) by 144 days.

(21) Appl. No.: 14/524,557

(22) Filed: Oct. 27, 2014

(65) Prior Publication Data

US 2015/0119762 A1    Apr. 30, 2015

Related U.S. Application Data

(63) Continuation of application No. PCT/JP2013/077004, filed on Oct. 3, 2013.
(Continued)

(51) Int. Cl.
*A61N 7/00* (2006.01)
*A61B 17/32* (2006.01)
(Continued)

(52) U.S. Cl.
CPC ........ *A61N 7/00* (2013.01); *A61B 17/320092* (2013.01); *A61B 2017/2825* (2013.01);
(Continued)

(58) Field of Classification Search
CPC .... A61B 17/320092; A61N 2007/0004; A61N 7/00
See application file for complete search history.

(56) References Cited

U.S. PATENT DOCUMENTS 3,597,582 A * 8/1971 Goode ............... A61B 18/1402
219/144
5,149,322 A * 9/1992 Nash .............. A61B 17/320758
604/110
(Continued)

FOREIGN PATENT DOCUMENTS

JP    A-11-318918     11/1999
JP    A-2000-509636    8/2000
(Continued)

OTHER PUBLICATIONS

International Search Report issued in International Patent Application No. PCT/JP2013/077004 dated Nov. 26, 2013 (with translation).
(Continued)

*Primary Examiner* — Julie A Szpira
(74) *Attorney, Agent, or Firm* — Oliff PLC

(57) ABSTRACT

A treatment device is constituted of: an ultrasonic vibration element unit; a probe unit that can be attached or detached by rotating the ultrasonic vibration element unit, transmits ultrasonic vibration generated by the ultrasonic vibration element unit to a distal end side, and gives a treatment; a handle unit that has the probe unit penetrating therethrough and is configured to hold the probe unit so that its distal end extends; and a protruding portion provided to prevent the probe unit and the handle unit from relatively revolving around an axis of the probe, the handle unit including the probe unit that transmits the ultrasonic vibration and being attachable to/detachable from the ultrasonic vibration element unit.

10 Claims, 8 Drawing Sheets

Related U.S. Application Data

(60) Provisional application No. 61/710,362, filed on Oct. 5, 2012.

(51) Int. Cl.
    *A61B 17/28* (2006.01)
    *A61B 90/00* (2016.01)

(52) U.S. Cl.
    CPC ... *A61B 2090/031* (2016.02); *A61B 2090/035* (2016.02); *A61B 2090/037* (2016.02); *A61B 2090/0811* (2016.02); *A61B 2090/0814* (2016.02); *A61N 2007/0004* (2013.01)

(56) References Cited

U.S. PATENT DOCUMENTS

| | | | |
|---|---|---|---|
| 5,810,859 A * | 9/1998 | DiMatteo | A61B 17/320068 604/22 |
| 6,206,844 B1 * | 3/2001 | Reichel | A61B 17/320068 600/121 |
| 2008/0183201 A1 | 7/2008 | Berberich | |
| 2009/0143797 A1 | 6/2009 | Smith et al. | |
| 2011/0151980 A1 | 6/2011 | Petroff | |
| 2012/0078278 A1 | 3/2012 | Bales, Jr. et al. | |
| 2012/0101493 A1 | 4/2012 | Masuda et al. | |

FOREIGN PATENT DOCUMENTS

| | | |
|---|---|---|
| JP | 2004-033565 A | 2/2004 |
| JP | A-2004-236984 | 8/2004 |
| JP | 2008-264565 A | 11/2008 |
| JP | 2009-514566 A | 4/2009 |
| JP | 2010-167084 A | 8/2010 |
| JP | A-2010-167204 | 8/2010 |
| WO | WO 98/37819 | 9/1998 |
| WO | WO 2011/089769 A1 | 7/2011 |
| WO | 2011/163570 A2 | 12/2011 |

OTHER PUBLICATIONS

Feb. 24, 2015 Office Action issued in Japanese Application No. 2014-539833.

Apr. 28, 2016 Extended Search Report issued in European Patent Application No. 13843742.1.

* cited by examiner

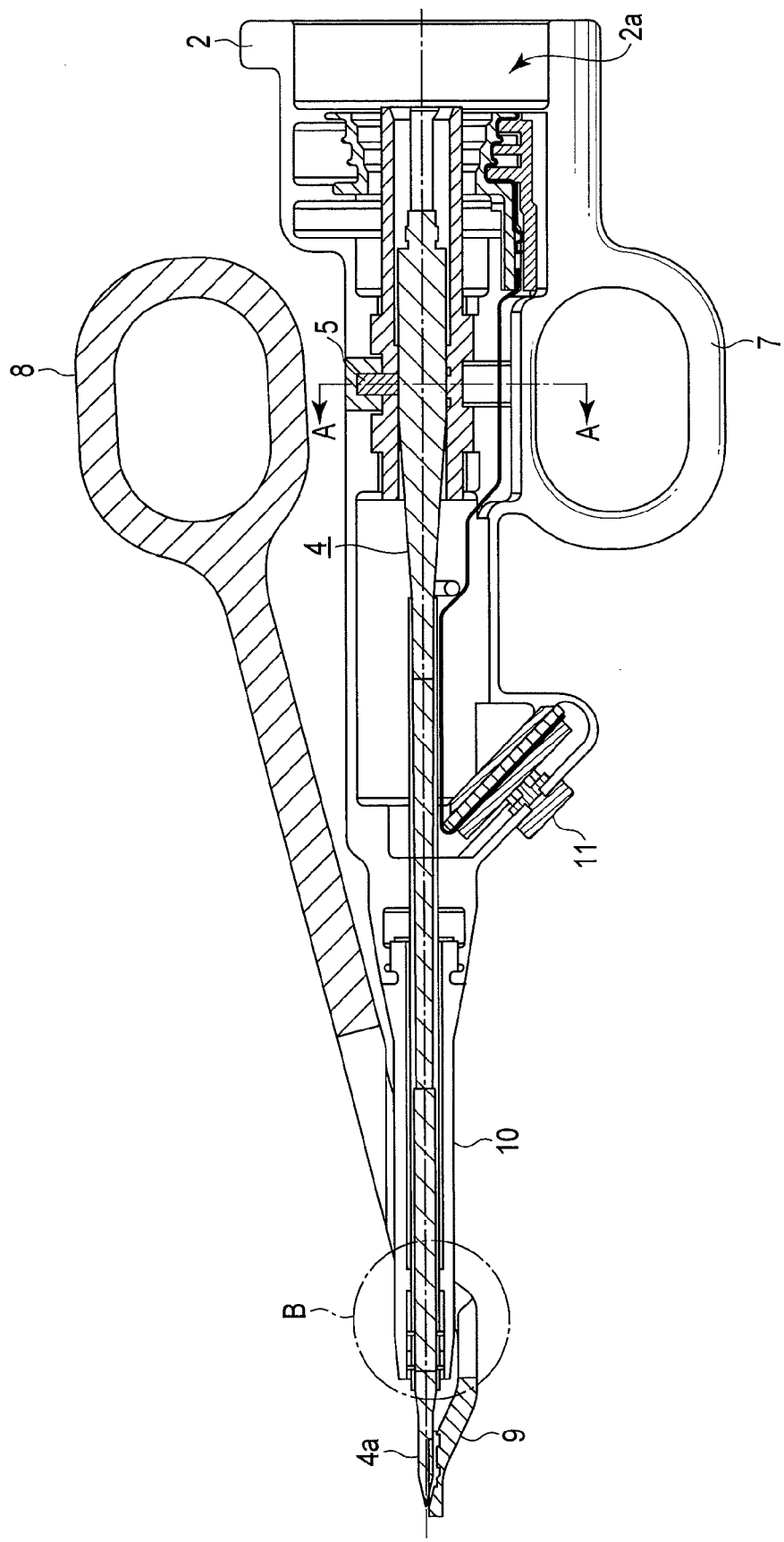
F I G. 2

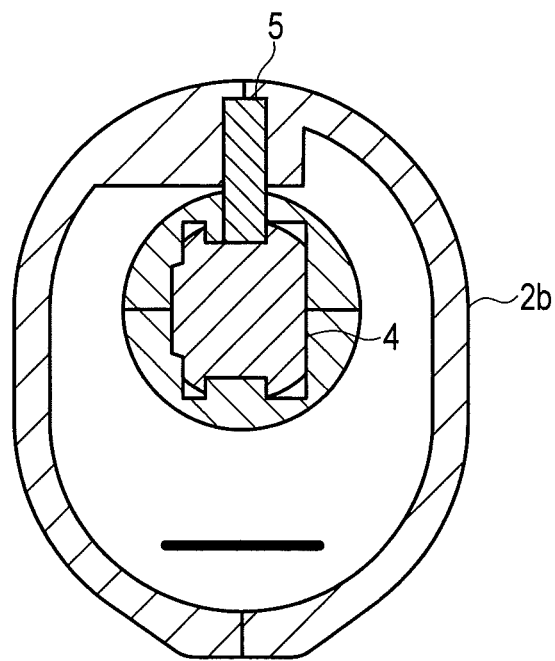
F I G. 3A
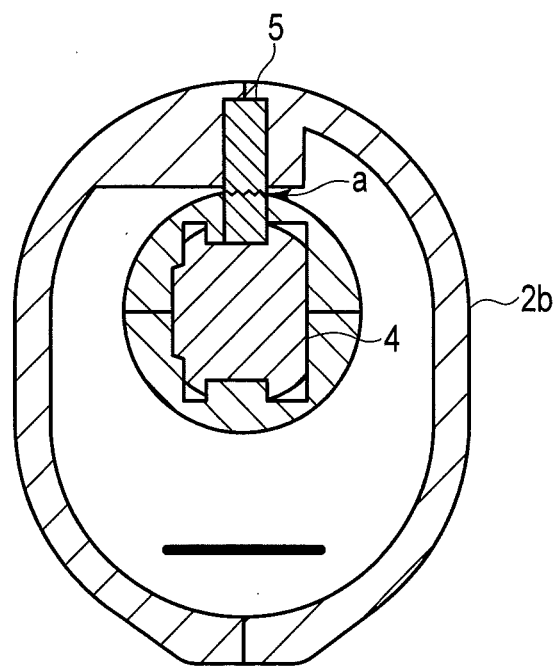
F I G. 3B

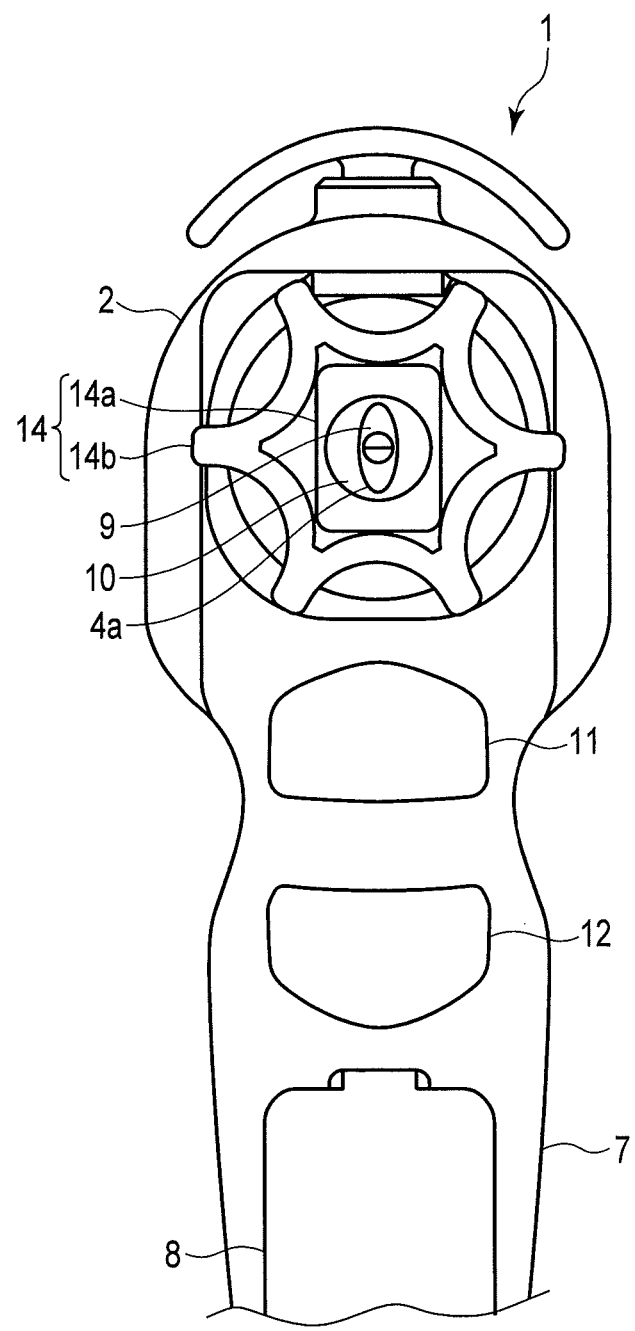
F I G. 6A

ULTRASONIC VIBRATION TREATMENT DEVICE

CROSS-REFERENCE TO RELATED APPLICATIONS

This is a Continuation Application of PCT Application No. PCT/JP2013/077004, filed Oct. 3, 2013, which was published under PCT Article 21(2) in Japanese. This application is based upon and claims the benefit of priority from prior the U.S. Patent Application No. 61/710,362, filed Oct. 5, 2012 the entire contents of which are incorporated herein by references.

BACKGROUND OF THE INVENTION

1. Field of the Invention

The present invention relates to a treatment device having an ultrasonic probe that gives a treatment using ultrasonic vibrations.

2. Description of the Related Art

In general, as a treatment device that incises and coagulates a target region of a living tissue or the like by using ultrasonic vibration, for example, such an ultrasonic vibration treatment device (which will be referred to as a treatment device hereinafter) as disclosed in USP No 2009/0143797A1 is known.

This treatment device is constituted of at least a transducer unit that generates the ultrasonic vibration and a handle unit to which a treatment section and a probe that transmits the ultrasonic vibration are disposed.

The handle unit that is in contact with a treatment target region (an affected part) is disposable because of sanitation for infectious diseases and others, and the transducer unit is disposed to a new handle unit and repeatedly used. Surgical operations using this treatment device have spread and have been generally conducted, and demands for the handle unit are increasing.

Therefore, there emerged vendors who disassemble, clean, reassemble, and resell used handle units that should be fundamentally discarded. They unrighteously acquire, disassemble, sterilize, reassemble, and reuse (resell) the used handle units. On the other hand, as regards to a handle unit that is partially damaged or broken, another handle unit is disassembled, and a necessary component is taken out, repaired, and reused.

Whether such a reuse product has essential performance relative to an unused genuine product or whether it is appropriately sterilized and sufficient in terms of a sanitary safety aspect is unclear. That is, there is widespread concern that a reuse product brings about patients' disadvantage. Therefore, a technique for preventing reuse of used handle units must be considered.

BRIEF SUMMARY OF THE INVENTION

According to an embodiment of the present invention, there is provided an treatment device comprising: an ultrasonic vibration element unit having an ultrasonic vibration element that generates ultrasonic vibration in response to supply of electric power; a probe unit that is attachable/detachable by rotating the ultrasonic vibration element unit and configured to transmit the ultrasonic vibration generated by the ultrasonic vibration element unit to a distal end side and give a treatment; a handle unit that has the probe unit penetrating therethrough and is configured to hold the probe unit so that its distal end extends; and a protruding portion provided to prevent the probe unit and the handle unit from relatively revolving around an axis of the probe.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a view showing a cross-sectional configuration of an ultrasonic vibration treatment device according to the first embodiment;

FIG. 3A is a view showing a cross-sectional configuration of a reuse preventing mechanism that is in an enabled state;

FIG. 3B is a view showing the cross-sectional configuration of the reuse preventing mechanism that is in a disabled state;

FIG. 6A is a view showing an appearance configuration when the ultrasonic vibration treatment device according to the second embodiment is seen from a distal end side;

DETAILED DESCRIPTION OF THE PREFERRED EMBODIMENT

Embodiments according to the present invention will now be described hereinafter with reference to the drawings.

First Embodiment

Figure 1:
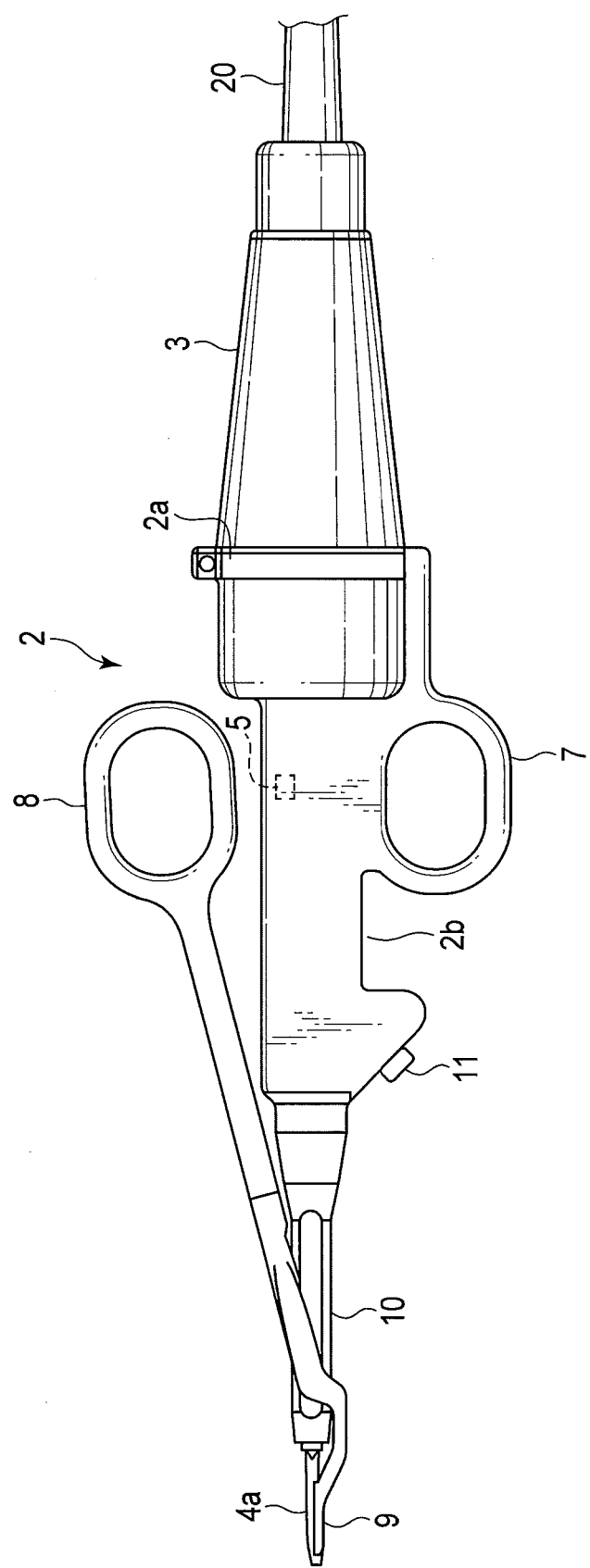
FIG. 1 is a cross-sectional view showing an appearance configuration of a treatment device having an ultrasonic probe including a reuse preventing mechanism mounted therein according to a first embodiment.

FIG. 1 is a cross-sectional view showing an appearance configuration of a handle unit in which an ultrasonic probe including a reuse preventing mechanism is mounted according to a first embodiment. FIG. 2 is a view showing a cross-sectional configuration of the handle unit (except a transducer unit (an ultrasonic vibration element unit)) according to the first embodiment.

A treatment device according to this embodiment gives treatments, e.g., incision, coagulation, and others using ultrasonic vibration. The treatment device 1 is constituted of a handle unit 2 having a treatment section that performs incision, coagulation, and others using the ultrasonic wave, a transducer unit 3 that generates the ultrasonic vibration, and a non-illustrated power supply unit that supplies driving power to the transducer unit 3. It is to be noted that the power supply unit is connected with the treatment device 1 through a power supply cable and supplies power for driving an ultrasonic vibration element, e.g., a piezoelectric element in the transducer unit 3 and a high-frequency signal (a signal having a current and a voltage each having an arbitrary high frequency). The high-frequency to be used is a frequency preferable for treatments, and it is not limited in particular unless otherwise legally restricted.

The handle unit 2 is used only once without being reused while taking sanitary or safety into consideration since a main body exterior thereof is made of, e.g., a resin material, an integrally provided treatment section directly comes into contact with a treatment target region, and a hand of an operator grips handles 7 and 8. On the other hand, since the transducer unit 3 does not directly come into contact with a treatment target region, it is subjected to a cleaning and sterilizing treatment and repeatedly+ used. It is to be noted that, in the following description, a later-described treatment section side is determined as a front side (or a distal end side) with respect to the handle unit 2 and a transducer unit 3 side is determined as a rear side.

The handle unit 2 is integrally constituted of a transducer mounting portion 2a, a unit main body 2b, a fixed handle 7, a pivotally supported movable handle 8, a probe unit 4, a sheath section 10, and a treatment section 9. The probe unit 4 is formed of an elongated conductor that extends through the inside of the unit main body 2b and propagates the ultrasonic vibration, and its outer peripheral surface is covered with the sheath section 10. The treatment section 9 is provided at a distal end of the probe unit 4.

The unit main body 2b is made of a resin material. The fixed handle 7 is integrally formed with the unit main body 2b and fixed. The movable handle 8 is pivotally supported on the distal end side of the sheath section 10 to allow its revolving motion.

The unit main body 2b is integrally formed by fitting at least two unit members (a housing). As shown in FIG. 1, the fixed handle 7 and the movable handle 8 are formed into a forceps shape or a scissors shape. The unit main body 2b is arranged to be sandwiched between these handles, and the unit main body 2b is integrally arranged on the fixed handle 7. The revolving treatment section 9 is, e.g., a jaw, and it is integrally provided with the movable handle 8 and holds a treatment target region between itself and a fixed probe distal end portion 4a.

A switch 11 that applies the ultrasonic vibration to the treatment section 9 is provided on the unit main body 2b ahead of the fixed handle 7. It is to be noted that the switch 11 is configured to be integrally provided on the unit main body in this embodiment, but the present invention is not restricted thereto, and a foot switch or the like may be separately used in place of this switch.

The transducer unit 3 has a well-known configuration in which the ultrasonic vibration element (e.g., the piezoelectric element) and a horn section are accommodated in the housing.

The transducer unit 3 is opened on the rear side of the handle unit 2 and manually screwed into the threaded mounting portion 2a. Furthermore, a non-illustrated torque wrench or the like is used and turned in, e.g., a mounting direction m in FIG. 3C to perform retightening so that a set value set at the time of design is realized. Performing screwing with the use of this torque wrench achieves an appropriate abutting state where the probe unit 4 and the horn section of the transducer unit 3 are appressed against each other, and the ultrasonic vibration is excellently transmitted to the probe unit 4. The probe unit 4 is covered with the sheath 10 at predetermined intervals except the distal end portion 4a provided at the distal end. The probe unit 4 extends through the unit main body 2b and propagates the ultrasonic vibration to the distal end portion 4a. Moreover, a non-illustrated annular elastic member such as a rubber ring is arranged at a node (non-vibration) portion of the ultrasonic vibration between the inner peripheral surface of the sheath 10 and the probe unit 4 so that mutual contact or interference is prevented from occurring.

In a state that the treatment section 9 is closed, an ultrasonic signal is transmitted from the probe distal end portion 4a. The probe unit 4 (which is substantially the sheath 10) is fixed in the unit main body 2b by using a support member at positions serving as the nodes of the ultrasonic vibration.

In such a configuration, after the treatment target region is held by the treatment section 9, a trigger signal is transmitted to a non-illustrated power supply section side by an ON operation of pressing the switch 11. The power supply section supplies the driving power to the ultrasonic vibration element (e.g., a piezoelectric element) to drive it, the generated ultrasonic vibration is applied to the distal end portion 4a and the treatment section 9 through the probe unit 4, and a desired treatment is given.

Then, when an OFF operation of returning the switch 11 is performed, the trigger signal is transmitted to the power supply section side, and driving of the ultrasonic vibration element is stopped. It is to be noted that the switch 11 may perform not only the ON/OFF control based on transmission of the trigger signal but also control over supply/stop of the driving power based on energization/non-energization of a switch contact (momentary) in a current circuit (a closed loop circuit) including the ultrasonic vibration element.

As shown in FIGS. 1 and 2, for example, a prism-shaped or plate-shaped protruding portion 5 that is fixed at a portion of the probe unit 4 corresponding to the node of the ultrasonic vibration in the unit main body 2b is provided. Although the protruding portion 5 may have a columnar shape, force used for cutting in a radial direction is large with respect to the prism, and hence a prism-like shape or a plate-like shape is preferable. It is to be noted that, when a set torque value of the torque wrench is not met or when a volume of an installing position is small and a thin protruding portion is demanded, a columnar shape may be adopted, and an outer shape, a cross-sectional area, and others may be appropriately set in accordance with an arrangement environment.

FIGS. 3A and 3B show a cross-sectional configuration of a portion A-A of the unit main body 2b depicted in FIG. 2.

As shown in these drawings, a bottom part of the protruding portion 5 is secured to and integrally coupled with the node portion of the probe unit 4, the protruding portion 5 extends partway in the housing of the unit main body 2b, and a top part thereof is configured not to be exposed on the exterior surface. At the time of creating the probe, the protruding portion 5 is also fabricated so that the ultrasonic vibration conforming to the design can be output. This protruding portion may be manufactured by using the same material as the probe unit 4 or may be manufactured by using a different material. For example, as shown in FIG. 3A, at the time of manufacturing the unit main body 2b, the protruding portion 5 is held together with the probe unit 4 by two unit members and accommodated to be fixed on both the probe unit 4 side and the unit member 2 side.

This protruding portion 5 has predetermined strength, and it is destroyed when force (or a load) exceeding its set value is applied thereto. Specifically, it cracks or bends. The strength is designed to withstand set torque that is applied when the torque wrench is hooked to perform retightening as described above. In general, since the wrench is used for manual tightening, tightening that reaches the set torque value cannot be performed, the torque wrench idles when a load higher than or equal to the set torque is applied. Therefore, since force having a value higher than or equal to the set torque is not applied, the strength of the protruding portion 5 can be set.

Figure 3C:
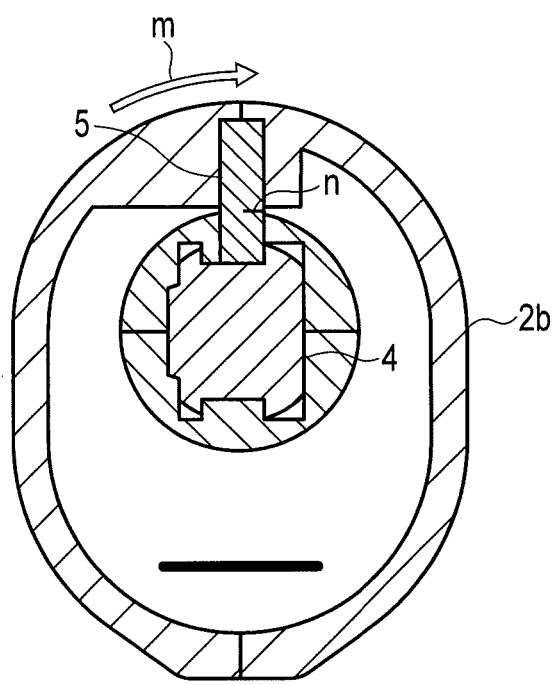
FIG. 3C is a view showing a cross-sectional configuration of a protruding portion of the reuse preventing mechanism.
Figure 3D:
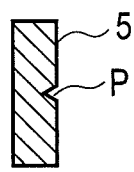
FIG. 3D is a view showing a cross-sectional configuration of a second example of the protruding portion of the reuse preventing mechanism.

As regards this strength setting, at the time of removing the transducer unit 3, a load exceeding the set torque is applied from an opposite direction (an opposite direction of a mounting direction m) of that at the time of mounting, and at least a crack or bending occurs at a position a of the protruding portion 5. Additionally, since a situation where the transducer unit 3 is removed with the set torque or lower torque can be also assumed, a cut n may be previously formed in a surface of the protruding portion 5 to which the load at the time of removal is applied as shown in FIG. 3C. Alternatively, as shown in FIG. 3D, a notch portion p formed of a V-shaped groove may be previously formed in the surface of the protruding portion 5 to which force at the time of removal is applied.

When the cut n or the notch portion p is formed in the surface to which the force at the time of removal is applied, the protruding portion 5 can withstand a load based on the set torque at the time of mounting without being damaged in case of mounting the transducer 3 to the mounting portion 2a. Contrarily, the force applied at the time of removing the transducer unit 3 assuredly causes a crack or bending in the protruding portion 5 from the cut n or the notch portion p. Further, the protruding portion 5 is fixed at the node position of the vibration in the probe unit 4. Since traction force is applied from both antinode (maximum amplitude) sides of the vibration, a crack or bending further easily occurs when the force is applied.

When the crack or bending has occurred in the protruding portion 5, oscillation characteristics in the probe unit 4 are affected. There are several causes and, for example, when the protruding portion 5 is damaged, its shape changes and its vibration characteristics also vary. Here, the vibration characteristics mean that at least an amplitude and a frequency of the vibration and positions of antinodes and nodes of the vibration on the probe change. Furthermore, since an entire volume of the probe changes, the vibration characteristics shift. When the protruding portion 5 is made of the same material as the probe unit 4, an impedance of the probe unit 4 changes, a load increases, and oscillation becomes impossible. It is to be noted that, usually, when a vibration frequency shifts or the impedance changes beyond a specified range, an abnormality is determined on the power supply side, and supply of power to the transducer unit 3 is stopped.

Moreover, when reuse is effected in a state that only a crack is formed in the protruding portion 5, this crack spreads or bending occurs due to the ultrasonic vibration propagated from the transducer unit 3 immediately before start of a treatment, and a disabled state is achieved.

As described above, according to this embodiment, a user can mount the transducer unit 3 to the handle unit 2 with the set torque by using the torque wrench without damage, and a crack or bending can be formed in the protruding portion constituting a reuse preventing mechanism at the time of removing the transducer unit 3. When this protruding portion is damaged, the oscillation characteristics are affected, and the reuse can be avoided. Additionally, the probe unit 4 may be rattled by damaging the protruding portion 5. Further, since removing the transducer from the handle unit 2 can damage the probe unit 4, an intentional operation performed by a user is not required. Furthermore, since the protruding portion is not exposed on the unit surface, it is not subject to the ultrasonic vibration, and safety is assured.

A modification of the first embodiment will now be described.

Figure 4A:
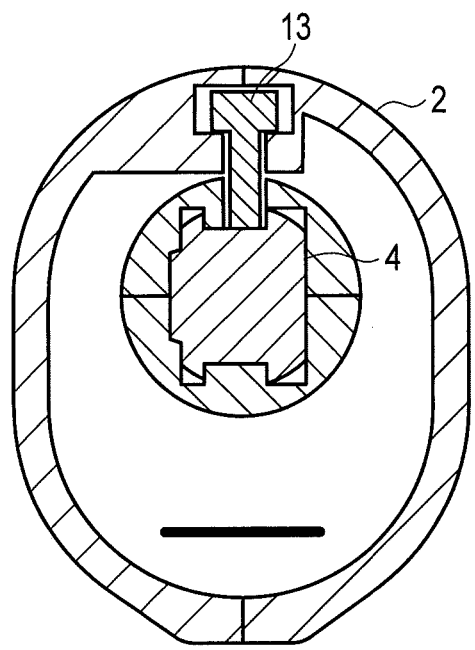
FIG. 4A is a view showing a cross-sectional configuration of a reuse preventing mechanism that is an enabled state according to a modification of the first embodiment.
Figure 4B:
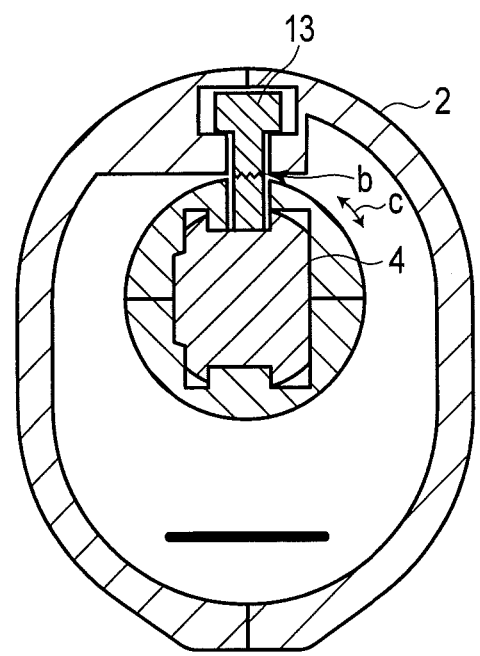
FIG. 4B is a view showing the cross-sectional configuration of the reuse preventing mechanism that is in a disabled state according to the modification of the first embodiment.

FIG. 4A is a view showing a cross-sectional configuration of a reuse preventing mechanism in an enabled state according to a modification, and FIG. 4B is a view showing a cross-sectional configuration of the reuse preventing mechanism in a disabled state.

In this modification, as shown in FIG. 4A, a protruding portion 13 has a T-like shape that a top part on the unit member 2 side projects into a flange shape. In this configuration, the projecting top part of the protruding portion 13 may be hooked on a member on the unit member 2 side and a columnar portion excluding the top part may be narrowed so that a gap can be formed between the protruding portion 13 and the member on the unit member 2 side. That is, the protruding portion 13 suspends the probe unit 4 without affecting the vibration characteristics of the probe unit 4. Furthermore, in a manufacturing accuracy of the protruding portion 13, since the gap may be formed between the protruding portion 13 and the unit member, the manufacturing accuracy becomes higher than that in the first embodiment.

In this configuration, in a case where the transducer unit 3 is removed from the handle unit 2 manually or with the use of a wrench or the like, when a crack is produced in the protruding portion 13 as shown in FIG. 4B, force that pulls down the protruding portion 13 is generated in the probe unit 4 by stress of suspension and acts on the crack to further spread, and a bent state can be easily realized.

As described above, this modification can provide functions and effects equivalent to those of the first embodiment. Moreover, the stress of suspending the probe unit 4 acts on the protruding portion 13, and the protruding portion 13 can be further easily bent after the crack is produced. Additionally, damaging the protruding portion 13 may rattle the probe unit 4.

Second Embodiment

Figure 5:
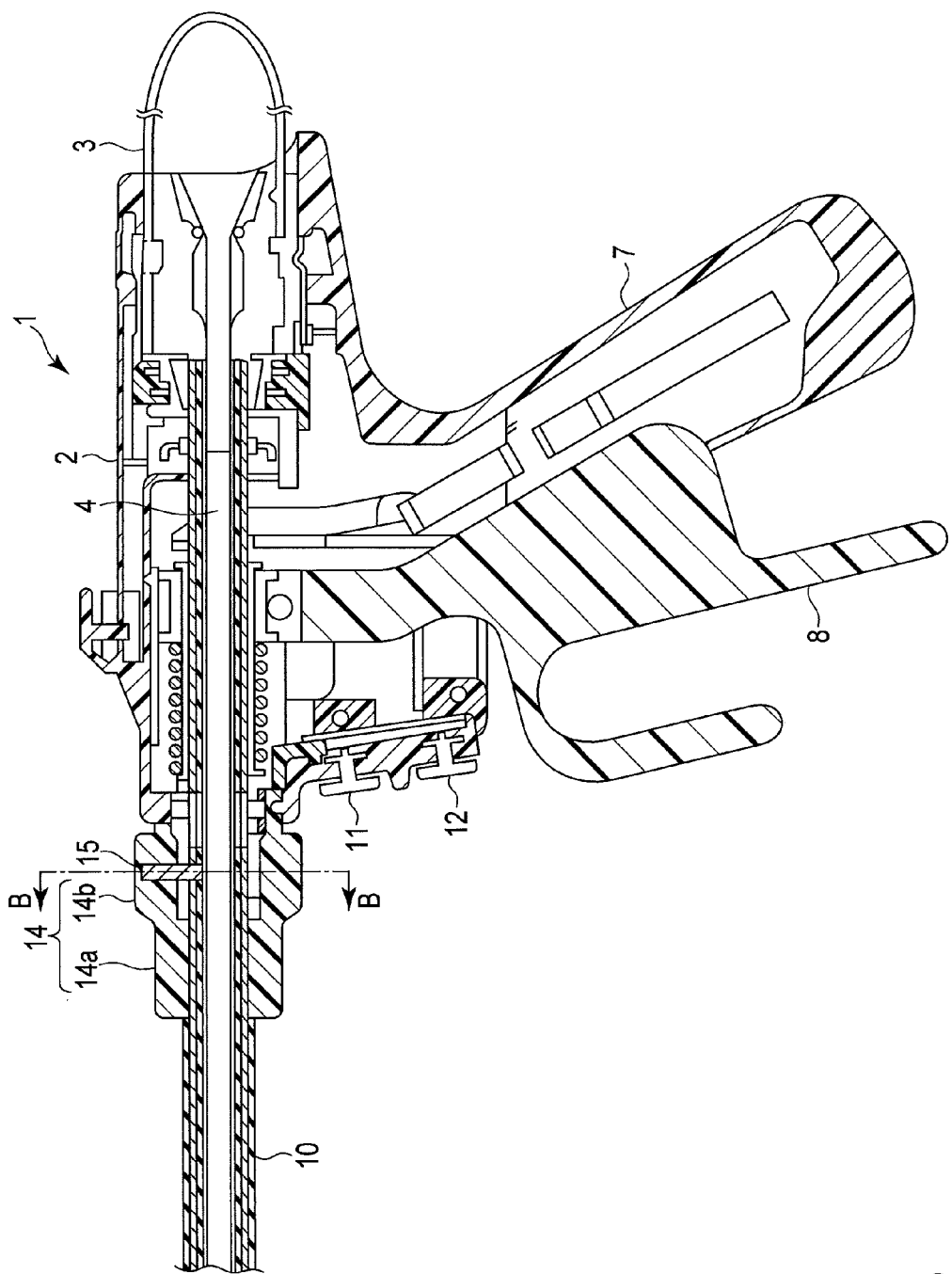
FIG. 5 is a view showing a cross-sectional configuration of an ultrasonic vibration treatment device according to a second embodiment.
Figure 6B:
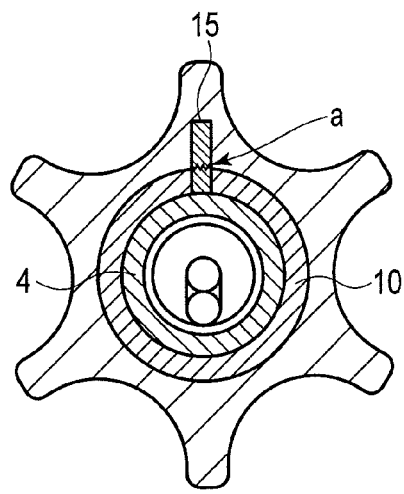
FIG. 6B is a view showing a cross-sectional configuration of a reuse preventing mechanism that is in a disabled state according to the second embodiment.

FIG. 5 is a view showing a cross-sectional configuration of an ultrasonic vibration treatment device according to a second embodiment. FIG. 6A is a view showing an appearance configuration when the ultrasonic vibration treatment device is seen from a distal end side, and FIG. 6B is a view showing a cross-sectional configuration of a reuse preventing mechanism in a disabled state taken along a B-B section in FIG. 5. It is to be noted that like reference numerals denote the same parts or parts having the same functions as those in the first embodiment to omit a description thereof.

A treatment device 1 has a pistol-like shape and is constituted of a disposable handle unit (a treatment device main body) 2 and a transducer unit 3 that is subjected to a sterilization treatment and repeatedly used. Further, electric power is supplied to the transducer unit 3 from a non-illustrated power unit through a power supply cable.

A handle section constituted of a fixed handle 7 and a movable handle 8 that serve as a grip is provided below a main body of the handle unit 2. The movable handle 8 is arranged on the front side of the fixed handle 7 and opens or closes a non-illustrated treatment section (a jaw) provided on a distal, end side of a sheath unit 10. This movable handle 8 is provided to enable its revolving motion around a fulcrum provided near a shaft side of the fixed handle 7 in the unit main body.

A probe unit 4 is mounted in the handle unit 2, and the probe unit 4 is covered with the sheath unit 10. The treatment section 9 formed of the jaw and a probe distal end portion 4a function as bipolar type high frequency electrodes when a high-frequency signal is applied.

Furthermore, a spring is fitted in the probe unit 4 and functions to energize the closed treatment section 9, and a held state of a treatment target region provided by the jaw 9 is maintained even if a gripping state of the movable handle 8 becomes slightly lose.

Figure 7:
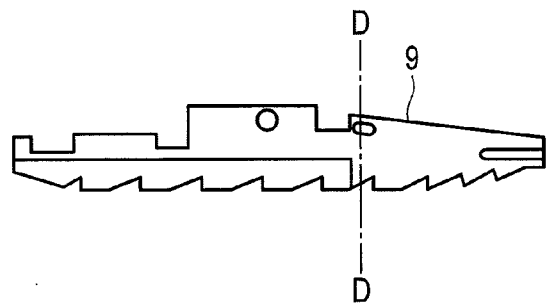
FIG. 7 is a view showing a configuration of a side surface of a jaw of a probe of a handle unit in which an ultrasonic probe including a reuse preventing mechanism is mounted according to a third embodiment.

A rotary knob 14 that revolves the probe unit 4 in a periaxial direction is provided on the distal end side of the handle unit 2. As shown in FIG. 6A, the rotary knob 14 is constituted of a mounting portion 14a on which a torque wrench is hooked at the time of mounting the transducer unit 3 and a dial portion 14b with which an operator performs an operation of rotating the treatment section. Like the protruding portion 5, a protruding portion 15 is integrally provided to the probe unit 4 at a node position in ultrasonic vibration. This protruding portion 15 is provided to be buried in in the dial portion 14b of the rotary knob 14 as shown in FIG. 7 and FIG. 6B. Since the protruding portion 15 is configured to be fixed to the rotary knob 14, when the rotary knob 14 is rotated, the probe unit 4 can be revolved in the periaxial direction.

Moreover, a switch 11 used for applying the ultrasonic vibration to the treatment section 9 is provided on the front side of the fixed handle 7 of the unit main body 2b. It is to be noted that, although a liquid supply and suction mechanism is not shown, a switch 12 is a switch used for supply and sucking a liquid.

Like the above description, the transducer unit 3 is manually screwed into the handle unit 2, and retightening is carried out with a set torque value by using the torque wrench. The protruding portion 15 is retightened without damage with respect to a load having the set torque value. At the time of removing the transducer unit 3 after use of the treatment device 1, the wrench is hooked on the mounting portion 14a of the rotary knob 14 and rotated in a removing direction. At this time, as shown in FIG. 6B, a crack or bending occurs in the protruding portion 15 at a position a near the probe unit 4 like the first embodiment.

As described above, according to this embodiment, functions and effects equivalent to those of the first embodiment can be provided. Additionally, to change a holding direction relative to a treatment target held between the probe distal end and the jaw, since the probe unit 4 is fixed to the rotary knob 14 that rotates the probe unit 4 by using the protruding portion 15, the rotating operation is also disabled by damaging the protruding portion 15.

A reference example will now be described hereinafter.

In the first and second embodiments, the protruding portion fixed to the probe unit is formed in the buried configuration so that it is not exposed on the outer peripheral surface of the handle unit 2. On the other hand, for example, the protruding portion can be extended to the unit surface and a knob cover formed into a knob shape can be secured so that the protruding portion itself is not exposed. In this configuration, the protruding portion may be twisted off from the probe unit by twisting the knob cover after use of the treatment device or at the time of discarding the treatment device. According to this configuration, whether the probe unit has been assuredly damaged at the time of removal can be visually confirmed.

Third Embodiment

A third embodiment will now be described.

Figure 8:
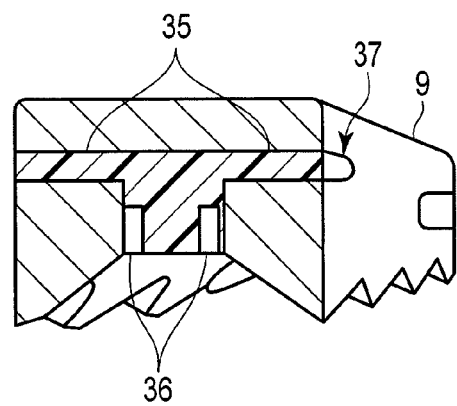
FIG. 8 is a view showing a configuration when a side including a jaw section of a section D-D in FIG. 7 is viewed from an oblique direction.

FIG. 8 is a view showing a configuration of a side surface of a jaw of a probe of a handle unit in which an ultrasonic probe including a reuse preventing mechanism is mounted according to a third embodiment, and FIG. 8 is a view showing a configuration when a side including a jaw section of a section D-D in FIG. 7 is seen from an oblique direction.

A jaw 9 having an alligator mouth-like shape is provided near a distal end portion of the probe to allow its opening and closing motions and holds a treatment target region between itself and the distal end portion of the probe. As shown in FIG. 9, a protruding portion to hold having an antiskid function using many protrusions for a target region to be held is formed around the periphery of a holding surface of the jaw 9, and a resin pad 37 made of a resin material (e.g., Teflon: a registered trademark) that has a substantially T-like shape, a buffering action, and excellent heat resisting properties is provided at the center of a concave portion. The resin pad 37 is a consumable that is consumed by constant use (e.g., coagulation and incision treatments using ultrasonic vibration) of a treatment section.

This resin pad 37 is manufactured by burying a resin material in the jaw 9, which has been subjected to hole drilling at the time of manufacture in advance, based on insert molding. At this time, shapes of spaces to filling (filling spaces) formed in the jaw 9, there are a shoulder space 35 extending in a lateral direction and a waist space extending from the center of the shoulder space 35 toward a lower side in a vertical direction.

Further, a convex portion 36 that protrudes inward is formed at part of the lower side of the waist space, and a step that projects inwards is provided. When the resin material is inserted into such filling spaces and formation is carried out, an inner cross section of a T-shaped connecting portion of the resin pad 37 is larger than a surface exposed on a lower surface of the same, and the resin pad is destroyed and taken out in case of taking it out from the outside. However, since the resin pad 37 is a component formed by the insert molding, its inner portion is larger than an opening surface on the lower surface, it is difficult to form the resin pad 37 outside and fitted it into the filling spaces. Therefore, to reuse the jaw 9, the resin material must be freshly used for the insert molding in the filling spaces to form the resin pad 37.

In this embodiment, the shape having the step provided inside is adopted but, besides this shape, it is also possible form an inverted trapezoidal shape that both sides of a root part of the T portion are narrowed toward the exposed surface.

As described above, according to this embodiment, the insert molding must be performed to form the resin pad serving as a consumable in the jaw 9. Reuse products do not have merits unless they can be reproduced at a low cost. Taking out and sterilizing the resin pad 37 and then again performing the insert molding take time and increase not only a manufacturing cost but also a labor cost. Thus, a high cost is required for reproduction, and a useful suppression effect can be brought about.

1) The treatment device is constituted of the ultrasonic vibration element unit and a handle unit that includes the probe unit which transmits ultrasonic vibration and is attachable to/detachable from the ultrasonic vibration element unit, and comprises the reuse preventing mechanism in which the protruding portion is erected at a node position of the ultrasonic vibration on the probe unit, its top part forms a prismatic shape fixed to the part of the handle unit, and a crack is included to cause destruction due to a load applied at the time of rotation in an operation of removing the ultrasonic vibration element unit from the handle unit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device comprising:
    an ultrasonic vibration element unit having an ultrasonic vibration element that generates ultrasonic vibration in response to a supply of electric power;
    a probe unit configured to transmit the ultrasonic vibration generated by the ultrasonic vibration element unit to a distal end side and give a treatment, the probe unit including a jaw and a probe distal end portion that open and close in an alligator mouth shape, and hold a treatment target region, the jaw including:
        a holding surface disposed opposite of the probe distal end portion, and
        a T-shaped resin pad penetrating through filling spaces, the T-shaped resin pad having: (i) an inner cross-section that is larger than an opening surface formed on the holding surface of the jaw, (ii) one end exposed in a center of the holding surface, and (iii) a portion of each of two opposite ends of the T-shaped resin pad extend in a lateral direction and each opposite end is exposed on a respective side surface of the jaw;
    a handle unit having the probe unit penetrating therethrough, the handle unit being configured to hold the probe unit in a revolvable state in a predetermined periaxial direction;
    a protruding portion preventing the handle unit from relatively revolving around an axis of the probe unit, the protruding portion being: (i) sandwiched between the handle unit and the probe unit, and (ii) fixed at a node position of vibration of the probe unit; and
    a damaged portion formed on the protruding portion positioned between the handle unit and the probe unit, the damaged portion including a cut portion or a notch portion in the predetermined periaxial direction.

2. The device according to claim 1, wherein
    the protruding portion has a top part and a bottom part, the top part being present inside a housing of the handle unit, the bottom part being integrally coupled with the probe unit, and
    the damaged portion is formed on a surface between the top part and the bottom part.

3. The device according to claim 2, wherein the damaged portion is formed on a surface of a side on which force is applied when the handle unit is revolved in a first periaxial direction of the probe unit when removing the probe from the handle unit.

4. The device according to claim 1, wherein the protruding portion has a prism-like shape or a plate-like shape.

5. The device according to claim 1, wherein a step or a taper is included in a surface that connects a surface exposed on the holding surface to a T-shaped root portion.

6. A treatment device comprising:
    a transducer having an ultrasonic vibration element configured to generate ultrasonic vibration;
    a probe configured to transmit the ultrasonic vibration generated by the transducer to a distal end side of the probe, the probe including a jaw and a probe distal end portion that open and close in an alligator mouth shape, and hold a treatment target region, the jaw including:
        a holding surface disposed opposite of the probe distal end portion, and
        a T-shaped resin pad penetrating through filling spaces, the T-shaped resin pad having: (i) an inner cross-section that is larger than an opening surface formed on the holding surface of the jaw, (ii) one end exposed in a center of the holding surface, and (iii) a portion of each of two opposite ends of the T-shaped resin pad extend in a lateral direction and each opposite end is exposed on a respective side surface of the jaw;
    a handle having the probe penetrating therethrough, the handle being configured to hold the probe in a revolvable state in a predetermined periaxial direction;
    a protruding portion preventing the handle from relatively revolving around an axis of the probe, the protruding portion being: (i) sandwiched between the handle and the probe, and (ii) fixed at a node position of vibration of the probe; and
    a damaged portion formed on the protruding portion positioned between the handle and the probe, the damaged portion including a cut portion or a notch portion in the predetermined periaxial direction.

7. The device according to claim 6, wherein
    the protruding portion has a top part and a bottom part, the top part being present inside a housing of the handle, the bottom part being integrally coupled with the probe, and
    the damaged portion is formed on a surface between the top part and the bottom part.

8. The device according to claim 7, wherein the damaged portion is formed on a surface of a side on which force is applied when the handle is revolved in a first periaxial direction of the probe when removing the probe from the handle.

9. The device according to claim 6, wherein the protruding portion has a prism-like shape or a plate-like shape.

10. The device according to claim 6, wherein a step or a taper is included in a surface that connects a surface exposed on the holding surface to a T-shaped root portion.

* * * * *